United States Patent
Moquin et al.

(10) Patent No.: US 10,525,231 B2
(45) Date of Patent: Jan. 7, 2020

(54) FLEXIBLE CATHETER

(71) Applicant: TRACTUS VASCULAR, LLC, Eatontown, NJ (US)

(72) Inventors: Craig Moquin, Fanwood, NJ (US); Andrew Filachek, Beechwood, NJ (US); Paige Reinhardt, Highlands, NJ (US); Matthew Koehler, Toms River, NJ (US); Darren De Medici, Middletown, NJ (US); Janet Burpee, Fair Haven, NJ (US)

(73) Assignee: TRACTUS VASCULAR, LLC, Eatontown, NJ (US)

( * ) Notice: Subject to any disclaimer, the term of this patent is extended or adjusted under 35 U.S.C. 154(b) by 166 days.

(21) Appl. No.: 15/515,806

(22) PCT Filed: Dec. 27, 2016

(86) PCT No.: PCT/US2016/068646
§ 371 (c)(1),
(2) Date: Mar. 30, 2017

(87) PCT Pub. No.: WO2017/117092
PCT Pub. Date: Jul. 6, 2017

(65) Prior Publication Data
US 2018/0326178 A1    Nov. 15, 2018

Related U.S. Application Data

(60) Provisional application No. 62/274,203, filed on Jan. 1, 2016.

(51) Int. Cl.
*A61M 25/00* (2006.01)
*A61M 25/01* (2006.01)
(Continued)

(52) U.S. Cl.
CPC ......... *A61M 25/0013* (2013.01); *A61B 17/22* (2013.01); *A61L 29/02* (2013.01);
(Continued)

(58) Field of Classification Search
CPC ........... A61B 2017/22034; A61B 2017/22035; A61B 2017/00309; A61B 2017/22094;
(Continued)

(56) References Cited

U.S. PATENT DOCUMENTS 2,515,365 A    7/1950  Zublin
5,108,411 A    4/1992  McKenzie, Jr.
(Continued)

FOREIGN PATENT DOCUMENTS

JP    2990070 B2    12/1999

OTHER PUBLICATIONS

Prashant, PU, "Current and emerging catheter technologies for percutaneous transluminal coronary angioplasty." Research Reports in Clinical Cardiology 2014:5 213-226.
(Continued)

*Primary Examiner* — Katherine H Schwiker
(74) *Attorney, Agent, or Firm* — Studebaker & Brackett PC

(57) ABSTRACT

A flexible, elongated catheter tube having distal and proximal ends and a laser cut section there between. The laser cut section makes up a majority of the catheter length and is cut in a continuous helical pattern forming interlocking teeth which can be sinusoidal, triangular, square or likes shapes, preferably sinusoidal. The interior of the catheter tube has a polymeric bi-layer of a nylon or like polymer at the interface of the tube interior and a Teflon or like polymer forms the interior lumen of the catheter. The exterior of the tube has a thin polymer coating of nylon or the like. A short portion of the distal end is uncut and is followed by a narrower terminal (Continued)

section which can be tapered for better blockage penetration. The interlocking teeth disengage and reengage in a fish scale manner without undergoing plastic deformation and without substantial polymer separation.

23 Claims, 15 Drawing Sheets

(51) Int. Cl.

| | | |
|---|---|---|
| A61B 17/22 | (2006.01) | |
| F16C 1/00 | (2006.01) | |
| F16C 1/02 | (2006.01) | |
| A61L 29/02 | (2006.01) | |
| A61L 29/04 | (2006.01) | |
| A61L 29/06 | (2006.01) | |
| A61L 29/08 | (2006.01) | |
| B23K 26/38 | (2014.01) | |
| B23K 103/00 | (2006.01) | |
| B23K 101/06 | (2006.01) | |
| A61B 17/00 | (2006.01) | |

(52) U.S. Cl.
CPC ........... *A61L 29/041* (2013.01); *A61L 29/049* (2013.01); *A61L 29/06* (2013.01); *A61L 29/085* (2013.01); *A61M 25/0054* (2013.01); *A61M 25/01* (2013.01); *A61M 25/0141* (2013.01); *B23K 26/38* (2013.01); *F16C 1/00* (2013.01); *F16C 1/02* (2013.01); *A61B 2017/00309* (2013.01); *A61B 2017/00526* (2013.01); *A61B 2017/00853* (2013.01); *A61B 2017/00867* (2013.01); *A61B 2017/22038* (2013.01); *A61B 2017/22094* (2013.01); *A61L 2420/08* (2013.01); *A61M 2205/0222* (2013.01); *A61M 2205/0238* (2013.01); *A61M 2205/0266* (2013.01); *B23K 2101/06* (2018.08); *B23K 2103/42* (2018.08); *F16C 2208/36* (2013.01); *F16C 2223/30* (2013.01); *F16C 2240/60* (2013.01); *F16C 2316/10* (2013.01)

(58) Field of Classification Search
CPC ....... A61B 2017/320024; A61B 2017/320032; A61B 17/32002; A61B 17/320016; A61B 17/1631; A61B 17/22; A61B 17/2231; A61B 2017/320028; A61B 2017/2905; A61B 2017/22037; A61B 2017/22038; A61B 2017/22039; A61B 2017/22041; A61B 2017/22095; A61M 25/0013; A61M 25/0054; A61M 25/0138; A61M 25/0171; A61M 2205/0238; A61M 2205/0266; A61M 25/0043; A61M 25/0045; A61M 25/0141; A61M 2025/0046; A61M 2025/0047
USPC ................................ 604/523–525, 534, 535
See application file for complete search history.

(56) References Cited

U.S. PATENT DOCUMENTS

| | | | |
|---|---|---|---|
| 5,334,145 | A | 8/1994 | Lundquist et al. |
| 5,437,288 | A | 8/1995 | Schwartz et al. |
| 5,573,520 | A | 11/1996 | Schwartz et al. |
| 5,683,640 | A | 11/1997 | Miller et al. |
| 5,747,429 | A | 5/1998 | Katoh et al. |
| 6,053,922 | A | 4/2000 | Krause et al. |
| 6,447,518 | B1 | 9/2002 | Krause |
| 6,652,508 | B2 | 11/2003 | Griffin et al. |
| 6,656,195 | B2 | 12/2003 | Peters et al. |
| 6,921,397 | B2 | 7/2005 | Corcoran |
| 7,300,430 | B2 | 11/2007 | Wilson et al. |
| 7,389,148 | B1 | 6/2008 | Morgan |
| 7,413,563 | B2 | 8/2008 | Corcoran et al. |
| 7,625,364 | B2 | 12/2009 | Corcoran et al. |
| 7,708,704 | B2 | 5/2010 | Mitelberg et al. |
| 7,763,012 | B2 | 7/2010 | Petrik et al. |
| 7,879,022 | B2 | 2/2011 | Bonnette et al. |
| 8,206,370 | B2 | 6/2012 | von Oepen et al. |
| 8,206,372 | B2 | 6/2012 | Larson et al. |
| 8,323,241 | B2 | 12/2012 | Salahieh et al. |
| 8,357,140 | B2 | 1/2013 | Majercak et al. |
| 8,366,559 | B2 | 2/2013 | Papenfuss et al. |
| 8,376,865 | B2 | 2/2013 | Forster et al. |
| 8,439,947 | B2 | 5/2013 | Howard et al. |
| 8,454,535 | B2 | 6/2013 | Majercak et al. |
| 8,632,556 | B2 | 1/2014 | Jacobs et al. |
| 8,758,231 | B2 | 6/2014 | Bunch et al. |
| 9,060,806 | B2 | 6/2015 | Mallik et al. |
| 9,078,740 | B2 | 7/2015 | Steiner et al. |
| 9,232,954 | B2 | 1/2016 | Steiner et al. |
| 9,233,255 | B2 | 1/2016 | Hebert |
| 9,295,807 | B2 | 3/2016 | Chin et al. |
| 2002/0038129 | A1 | 3/2002 | Peters et al. |
| 2003/0032970 | A1* | 2/2003 | Hiltebrandt ...... A61B 17/32002 606/170 |
| 2005/0080400 | A1 | 4/2005 | Corcoran et al. |
| 2006/0064123 | A1 | 3/2006 | Bonnette et al. |
| 2006/0084839 | A1 | 4/2006 | Lentz |
| 2006/0084939 | A1 | 4/2006 | Lentz |
| 2006/0142696 | A1 | 6/2006 | Kumoyama et al. |
| 2007/0088323 | A1* | 4/2007 | Campbell ............ A61M 25/10 604/523 |
| 2008/0147001 | A1* | 6/2008 | Al-Marashi ............ A61F 2/915 604/103.04 |
| 2009/0099554 | A1 | 4/2009 | Forster et al. |
| 2010/0241154 | A1 | 9/2010 | Larson et al. |
| 2010/0331776 | A1 | 12/2010 | Salahieh et al. |
| 2011/0152880 | A1 | 6/2011 | Alvarez et al. |
| 2012/0265229 | A1 | 10/2012 | Rottenberg et al. |
| 2012/0303005 | A1 | 11/2012 | Forster et al. |
| 2014/0031843 | A1 | 1/2014 | Rottenberg et al. |
| 2014/0114288 | A1* | 4/2014 | Beasley ............ A61M 25/0054 604/525 |
| 2014/0135736 | A1 | 5/2014 | Hebert |
| 2014/0148787 | A1 | 5/2014 | Forster et al. |
| 2014/0235361 | A1 | 8/2014 | Forster et al. |
| 2014/0277009 | A1 | 9/2014 | Mallik et al. |
| 2014/0283355 | A1 | 9/2014 | Chin et al. |
| 2015/0094656 | A1* | 4/2015 | Salahieh ........... A61M 25/0141 604/95.04 |
| 2015/0374398 | A1* | 12/2015 | Tobis ............... A61B 17/32002 606/171 |
| 2016/0082225 | A1* | 3/2016 | Kobayashi ........ A61M 25/0013 604/523 |

OTHER PUBLICATIONS

Javed, U, and Laird, JR, "Specialty Crossing Devices: Understanding the Learning Curve," Endovascular Today May 2012: 52-57.
Banerjee, A, and Brilakis, ES,"Coronary Chronic Total Occlusion Interventions," American College of Cardiology, Jun. 9, 2015, 11 pages, accessed Mar. 16, 2017 at http://www.acc.org/latest-in-cardiology/articles/2015/06/09/13/31/coronary-chronic-total-occlusion-interventions.
Sianos,G, Konstantinidis, N, Di Mario, C and Karvounis, H, "Theory and practical based approach to chronic total occlusions," Cardiovascular Disorders (2016) 16:33, 1-11.
U.S. Food and Drug Administration. 510(k) Summary. K072724. Nov. 9, 2007. 5 pages. Searchable 510(k) Database. Web. Accessed Mar. 24, 2017. <http://www.accessdata.fda.gov/cdrh_docs/pdf7/K072724.pdf>.
U.S. Food and Drug Administration. 510(k) Summary. K033678. Feb. 23, 2004. 5 pages. Searchable 510(k) Database. Web. Accessed Mar. 24, 2017. <http://www.accessdata.fda.gov/cdrh_docs/pdf7/K033678.pdf>.

(56) References Cited

OTHER PUBLICATIONS

U.S. Food and Drug Administration. 510(k) Summary. K133539. Mar. 26, 2014. 7 pages. Searchable 510(k) Database. Web. Accessed Mar. 24, 2017. <http://www.accessdata.fda.gov/cdrh_docs/pdf7/K133539.pdf>.
Thomas, International Search Report and Written Opinion of PCT/US2016/068646, 18 pages (dated Mar. 2017).

* cited by examiner

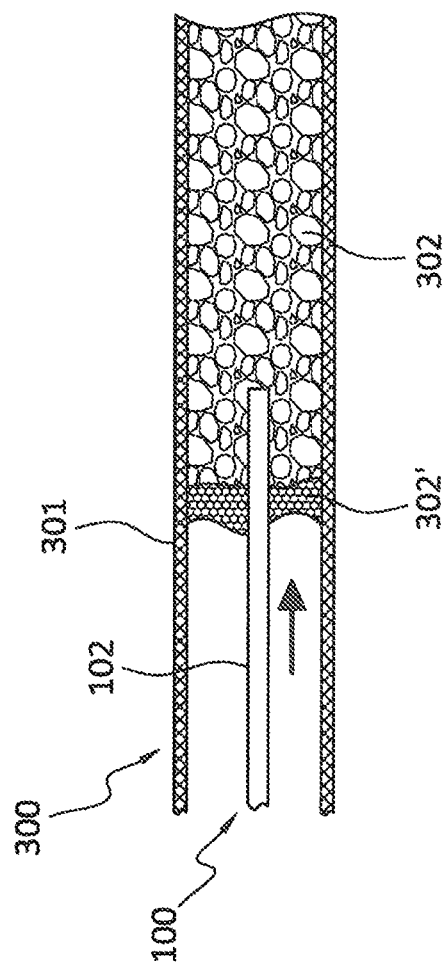
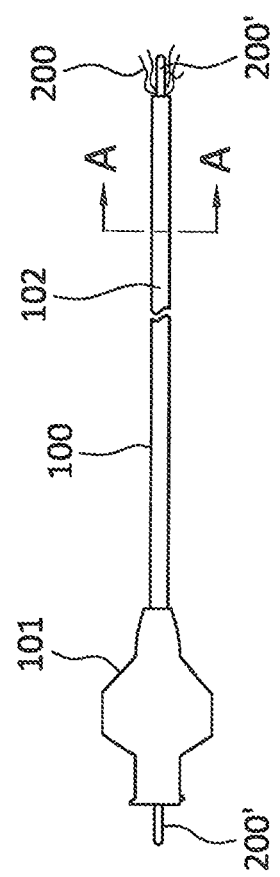
FIG. 5
FIG. 6

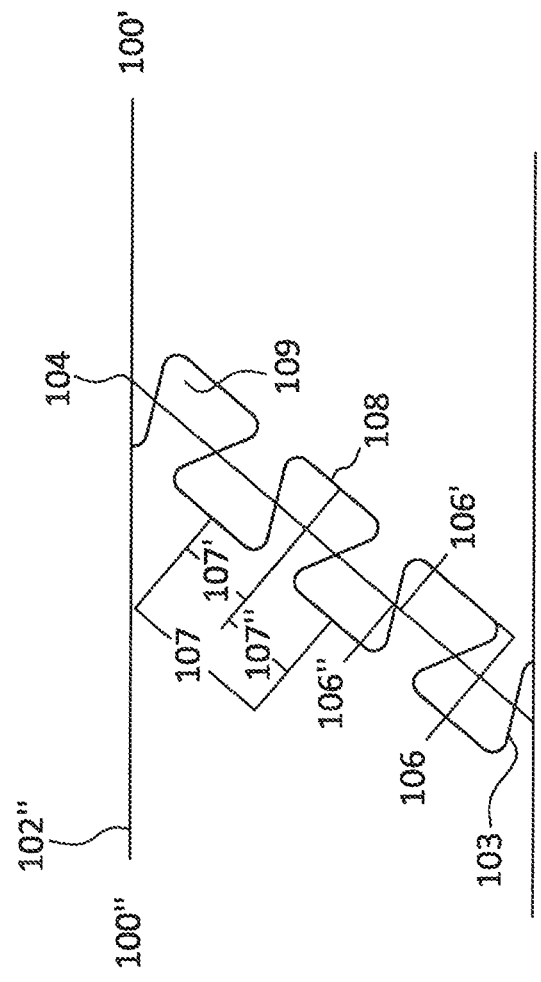
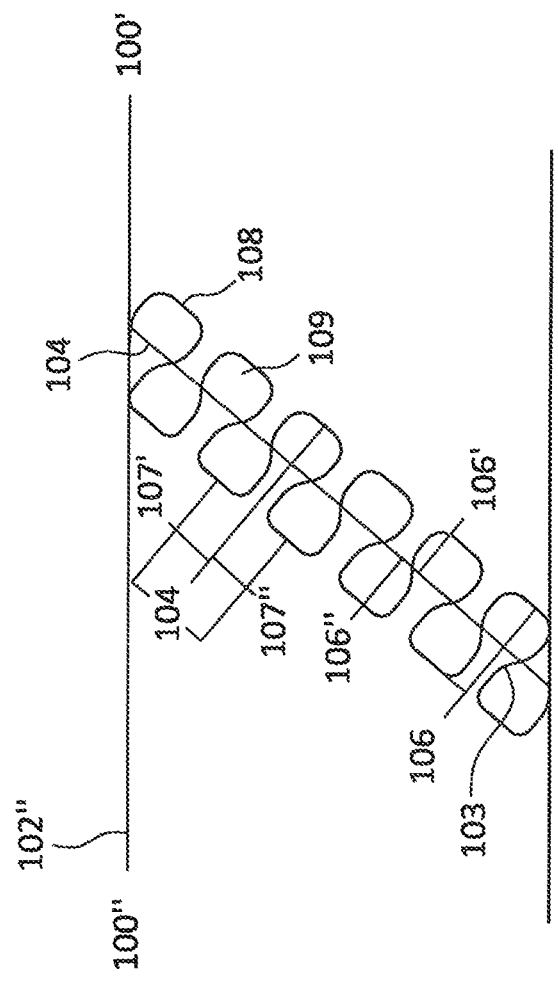
FIG. 12
FIG. 13

FLEXIBLE CATHETER

CROSS-REFERENCE TO RELATED APPLICATIONS

The present application claims priority on prior U.S. Provisional Application Ser. No. 62/274,203, filed Jan. 1, 2016, which is hereby incorporated herein in its entirety by reference.

FIELD OF THE INVENTION

This invention relates to a flexible catheter tube which is capable of transmitting rotary and axial motion to resolve blockages in a body lumen such as a blood vessel.

BACKGROUND OF THE INVENTION

For well over fifty years, there has been a need to create a flexible tube from an otherwise stiff tube by cutting the tube along the length. There are many examples of this design approach for many instruments in medical devices including catheters and guidewires (U.S. Pat. No. 5,573,520), bone reamers (U.S. Pat. Nos. 5,108,411 and 6,053,922) and other non-medical applications such flexible drill bores for well drilling (U.S. Pat. No. 2,515,365).

Flexible shafts and couplings are used to transmit rotary power between a power source and a driven part when a straight, unobstructed path is unavailable. A flexible shaft generally consists of rotating shaft with end fittings for attachment to mating parts which together construct a device. The power source is anything which can transmit the correct forces including a motor or a physician's hand. The shaft is envisioned to be used to transmit motion in a curvilinear manner such as a catheter shaft delivered through the iliac arch in the hip region, or for use as a bone reamer with flexible medullary canal reamers.

Historically, flexible shafts have been comprised of braided wire, slotted tubing, wound wire, or small diameter polymer tubing. Small diameter polymer tubing is not considered an ideal option for some applications due to a lack of pushability and high risk of kinking. This ability to transmit energy from one end of the shaft to the other is considered one of the most important characteristics when maneuvering through long, tortuous vessels. Hypotube-based shafts with a slotted or spiral cut pattern can extend the traditional limits of metal shafts, but continue to present limitations with flexibility and torque transmission. The traditional spiral cut pattern, for example, tends to wind up when torqued such that a one revolution turn at the torqued, or proximal end does not equal a one revolution turn at the non-torqued or distal end; in the worst cases, a one revolution turn results in a less than one-quarter of a revolution or less. The standard slotted pattern with no or limited male-female portion has better torqueability, but often limited bend radius along one or more planes.

Catheters and guidewires can include a full or portion of a shaft that is both flexible and torqueable or has a gradient of flexibility and torqueability along the length of the shaft. For optimal steerability and pushability, most catheter designs must have a maximum torsional rigidity while retaining a satisfactory kink-resistance and flexibility. These shafts can be used in many catheters and introducers including those for balloon angioplasty, stent delivery, electrophysiology applications, drug delivery or infusion, atherectomy, crossing catheters, or endovascular surgery. Depending on the application, the optimized and gradation of the flexibility and torqueability can be further modified by having a tube within a tube where the inside or outside tube or both can be comprised of a cut tube of this invention.

Chronic total occlusion (CTO) remains one of the most challenging pathologies encountered by surgeons and interventionalists alike. CTO is characterized by heavy atherosclerotic plaque burden resulting in complete, or near complete occlusion of a vessel for at least 1-3 months. CTO can occur in any part of the arterial vasculature, however, it is most common in the legs and other arteries near the heart. Chronic occlusions are present in up to 40% of patients who undergo treatment of symptomatic peripheral artery disease (PAD) and have been cited as one of the primary reasons for procedural failures. PAD is a prevalent condition, affecting about 10 million individuals in the United States and over 27 million individuals worldwide. CTO is also prolific in patients with coronary artery disease (CAD), the number one cause of death in the U.S. in both men and women, killing over 400,000 each year. Approximately 30% of all coronary angiograms in patients with coronary artery disease will show a CTO.

Restoring blood flow to the affected area is essential for improving blood supply and tissue perfusion to prevent limb amputation, heart failure and other clinical symptoms associated with these diseases. There are presently two predominate treatment strategies for CTO: bypass surgery or percutaneous recanalization. Until recently, CTOs of the coronary arteries were almost entirely referred for coronary artery bypass graft (CABG) procedures, or many were left untreated because of the high risk and uncertainty regarding CABG success rates. With a failure rate of up to 30%, recanalization poses its own set of technical challenges. A tough, fibrous cap is often present at the proximal and distal ends of the CTO with softer material in between. The majority of recanalization failures are due to an inability to cross the occlusion with the guidewire and balloon technologies currently available. Despite these challenges percutaneous revascularization has been associated with reduced angina, improved left ventricular function, reduced arrhythmias, and reduced mortality. Further innovations and refinement of current crossing catheter technologies are essential to increase procedural success in crossing long, calcified CTOs. Although the worst case for crossing a blocked vessel may be crossing one with a CTO, the intent of the invention is also for use for partial occlusions or simply crossing tortuous anatomy since the given construction can enable optimal performance in many applications.

SUMMARY OF THE INVENTION

The invention provides a flexible, elongated catheter tube having distal and proximal ends and a laser cut section therebetween. The laser cut section makes up a majority of the catheter length and is cut in a continuous helical pattern forming interlocking teeth which can be sinusoidal, triangular, square or likes shapes, preferably sinusoidal, wherein: (i) the interlocking teeth have a diameter of about 0.005 to about 0.015 inch, preferably from about 0.007 to about 0.015 inch; (ii) the helical angle of the center-line of the laser cut is a constant angle between about 64° and about 75°; (iii) the pitch between adjacent rows of teeth is in the range of about 0.028 to about 0.057 inch; (iv) the diameter of said teeth, the helical angle and the pitch resulting in from 4 to 12 repetitions of the teeth around the circumference of the laser cut section; and (v) the outside diameter of the tube is in the range of about 0.010 to about 0.052 inch and the wall thickness is about 0.001 to about 0.005, preferably 0.0015 inch.

The interior of the catheter tube has a polymeric bi-layer of a nylon or like polymer at the interface of the tube interior and a Teflon or like polymer forms the interior lumen of the catheter. The exterior of the tube has a thin polymer coating of nylon or the like.

The proximal end of the catheter is uncut and configured for coupling to a luer connection. A short portion of the distal end is also uncut and is followed by a narrower terminal section about 0.149 inch or less in length which can be tapered for better blockage penetration.

In operation, the interlocking teeth disengage and reengage in a fish scale manner without undergoing significant plastic deformation and without substantial polymer separation when the catheter is flexed as it travels through a body lumen such as a blood vessel. The catheter is thus capable of transmitting an axial, push force against a vascular occlusion to cross same and allow the catheter to advance beyond the occlusion.

The invention also provides a process for resolving partial or total body lumen blockages or occlusions which includes inserting the catheter described above into body lumen having a blockage at a distal location and advancing the catheter through the body lumen until said distal end encounters the blockage. The interlocking teeth disengage and reengage in a fish scale manner without undergoing plastic deformation and without substantial polymer separation when the catheter is flexed during advancement thru the body lumen. An axial push force is transmitted from the proximal end of the catheter to the distal end to cross the blockage and allow the catheter to advance there beyond.

The invention further provides catheter tube which in cross section has an inside diameter of not less than about 0.010 inch, a polymeric bi-layer of a nylon polymer at the interface of the tube interior, a Teflon polymer forming the interior lumen of the catheter and a thin polymer exterior coating of a nylon or like polymer. The wall thickness of the catheter with inner layers and an outer coating is about 0.0015 to 0.010, preferably 0.007 inch.

DESCRIPTION OF THE DRAWINGS

The invention will be more fully understood from the following description and drawings wherein:

FIG. 5 is the same schematic as FIG. 4 showing the catheter of the invention crossing a dense end cap and entering the blockage;

FIG. 6 is a schematic diagram of the catheter of FIG. 1 having a luer fitting—attached to the proximal end of the catheter to allow flushing of the catheter prior to use;

FIGS. 11-17 depict alternate cut patterns for forming interlocking teeth; and

DETAILED DESCRIPTION OF THE INVENTION

Figure 1:
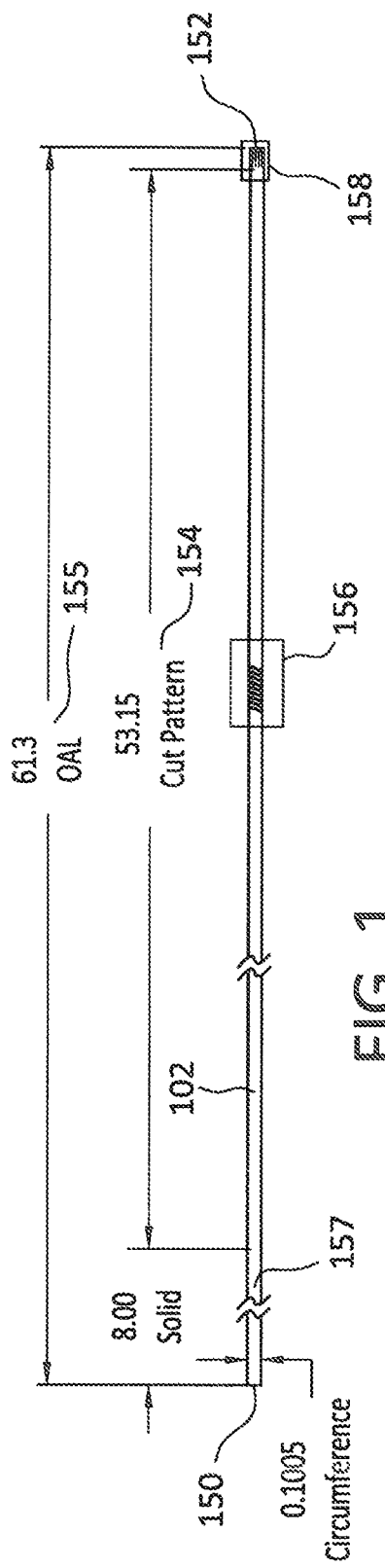
FIG. 1 is a diagrammatic side view of a catheter tube with dimensions of a preferred embodiment by way of example (all dimensions are in inches unless noted otherwise)

The catheter of the invention provides an unexpected and surprising combination of flexibility and the ability to deliver an axial push force greater than heretofore possible against an occlusion or total blockage to cross same and allow the catheter to advance there beyond. Flexibility allows an interventional radiologist using the inventive catheter to apply a twisting force or torque while pushing the catheter forward and follow a tortuous path in a body lumen (such as the iliac arch) without kinking. The distal section can be straight or angled as is known in the art.

Once kink-free delivery of the distal end to the point of a blockage or an occlusion is accomplished, the radiologist needs to apply axial pressure against the blockage to pass through or cross same to deliver a stent or other device to resolve the occlusion or blockage. For example, calcified lesions in an artery, known as chronic total occlusions (or CTOs) often have end caps that can be significantly harder to pierce or cross than the center of a CTO.

The catheter of the invention has demonstrated the ability to cross CTOs, even those with denser end caps, by exerting an axial push force in excess of 0.15 pounds and as high as one pound and more which is greater that heretofore possible with known catheters of comparable size. The inability to cross a CTO often leads to alternate and often riskier procedures (like open-heart surgery) to resolve a CTO.

The inventive catheter gives the radiologist several options for resolving a blockage. Once a guidewire locates a blockage, the inventive catheter can be inserted over the guidewire. A short section of the guidewire protruding from and supported by the catheter can challenge the CTO, or the distal end of the catheter and guidewire can be coextensive when pushed against a blockage or the guidewire can be withdrawn and the necked-down end of the catheter can be pushed through a CTO.

The structural parameters of the catheter of the invention are critical in achieving kink-free torquing and sufficient axial force to cross body lumen blockages. For example, the interlocking sinusoidal teeth must be able to disengage and reengage for flexibility without plastic deformation. Lesser values for teeth diameter and the pitch between rows of teeth can provide flexibility, and therefore better torque response around a bend, but at a cost of catheter buckling and decreased transmission of axial force. Exceeding the same values introduces undesirable stiffness and the inability to traverse tortuous body lumens. The use of interior and exterior polymer coatings (which may extend into, interface or blend with each other through the laser cut lines) aid in allowing the teeth to unlock (flex) and interlock without plastic deformation. Thus, smaller teeth may aid flexibility but easily deform; larger teeth resist unlocking and lead to undesirable stiffness.

Referring now to the drawings, FIG. 6 shows the inventive catheter generally indicated at 100. Catheter 100 includes a laser cut catheter tube 102 having a luer fitting 101 attached at the proximal end thereof to allow flushing of the catheter prior to use. Catheter 100 is capable of accepting ancillary devices typically used in endovascular and related medical procedures such guidewire 200' which is used to track catheter 100 to the target treatment area in a body lumen or to inject contrast fluid 200 through the catheter to enable imaging during a procedure.

Figure 7:
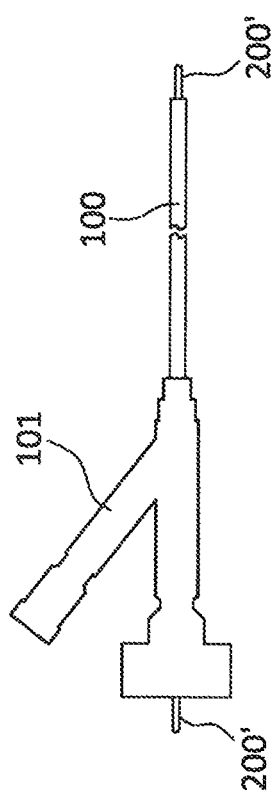
FIG. 7 is an alternate embodiment to FIG. 6 wherein the proximal luer is bifurcated to facilitate the delivery of multiple ancillary devices during a medical procedure.

FIG. 7 is similar to FIG. 6 wherein the proximal luer 101 is bifurcated to facilitate the delivery of multiple ancillary devices 200' through catheter 100 during a medical procedure.

Figure 4:
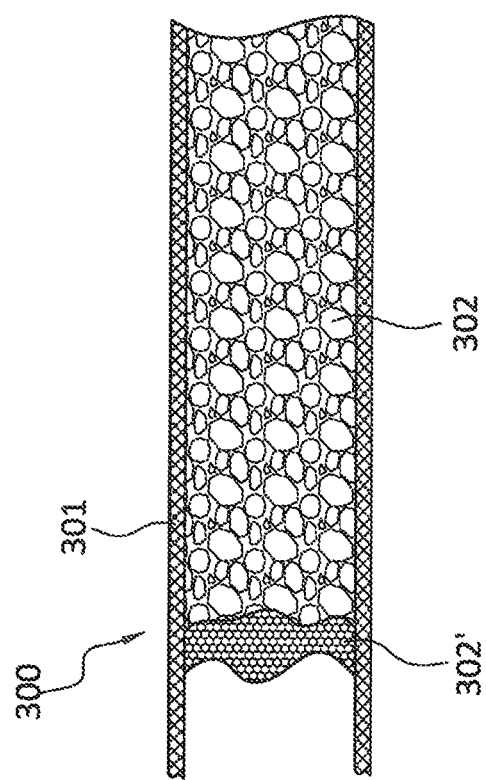
FIG. 4 is a schematic of a diseased artery with a total blockage including a denser end cap.

FIG. 4 shows a diseased artery 300 comprised of an arterial wall 301 and a heavily calcified lesion 302 known as a chronic total occlusion (CTO) which is typically comprised of denser end caps 302' on the proximal and distal ends that are significantly harder to access than the center of CTO 302.

FIG. 5 shows the distal end of catheter 100 crossing CTO 302 shown in FIG. 4. In order to cross the lesion, catheter 100 is capable of transmitting adequate force to the distal end when being pushed at the proximal and transmit adequate torque to the distal end when torque is applied to the proximal end. Catheter 100 is flexible enough at the distal end to navigate tortuous anatomies of the vasculature in order to reach the target site as well as be able to transmit force and torque in this configuration.

Figure 1A:
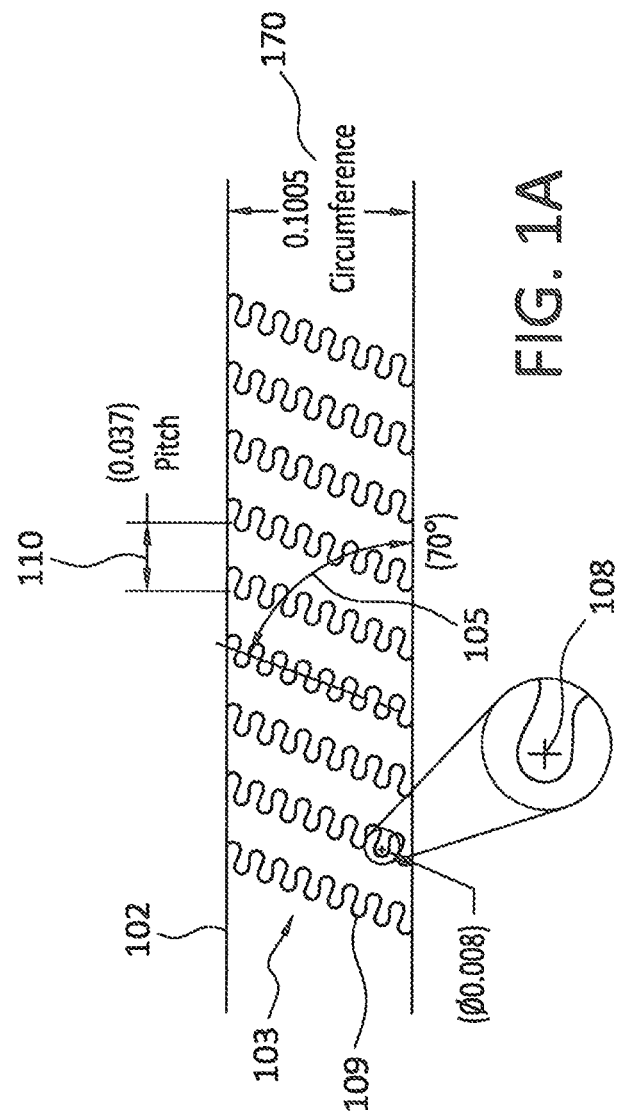
FIG. 1A is an exploded side view of a portion of the cut pattern shown in FIG. 1 with dimensions of a preferred embodiment by way of example.
Figure 1B:
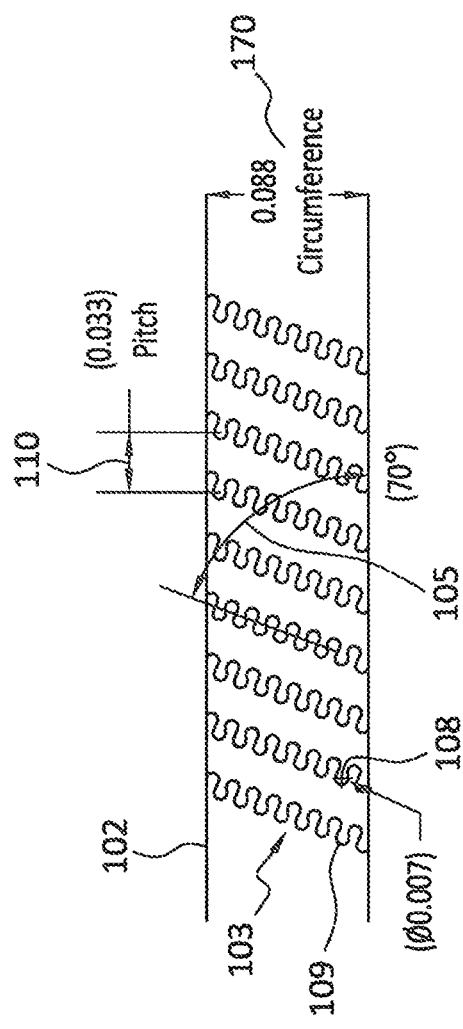
FIGS. 1B-D are exploded side views of alternate cut patterns for use in the catheter of FIG. 1 with dimensions by way of example.
Figure 1C:
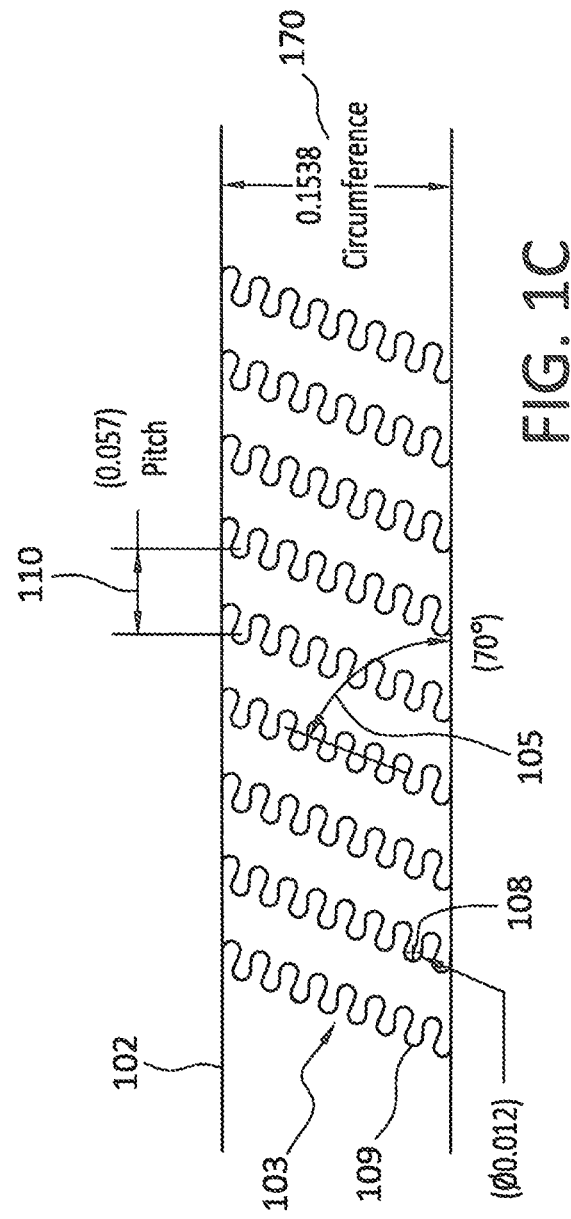
Figure 1D:
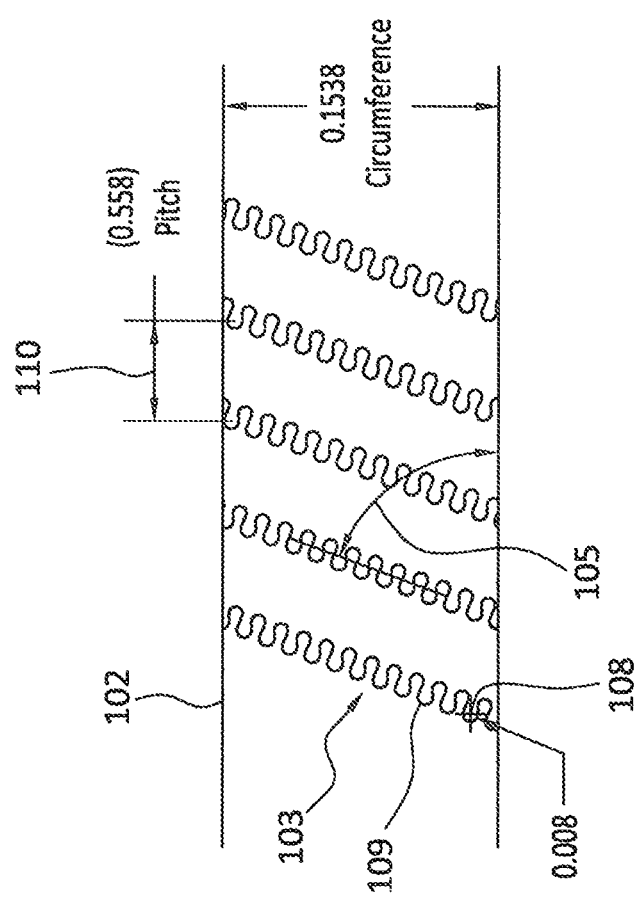
Figure 1E:
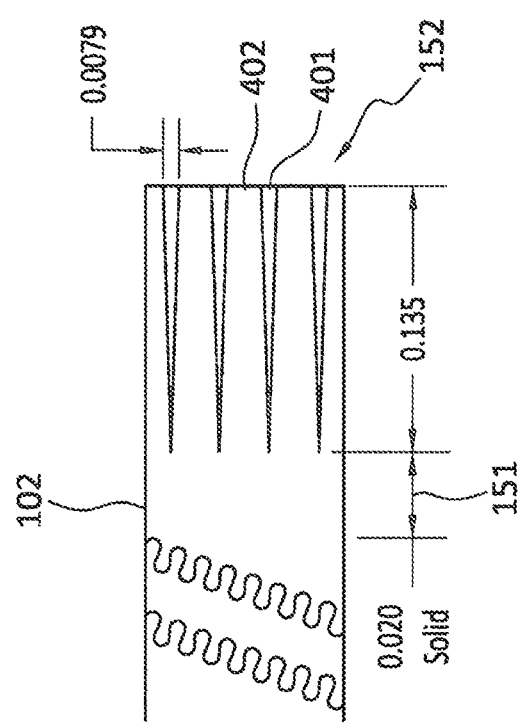
FIG. 1E is an exploded side view showing details of the distal end of the catheter of FIG. 1 with dimensions by way of example.
Figure 2:
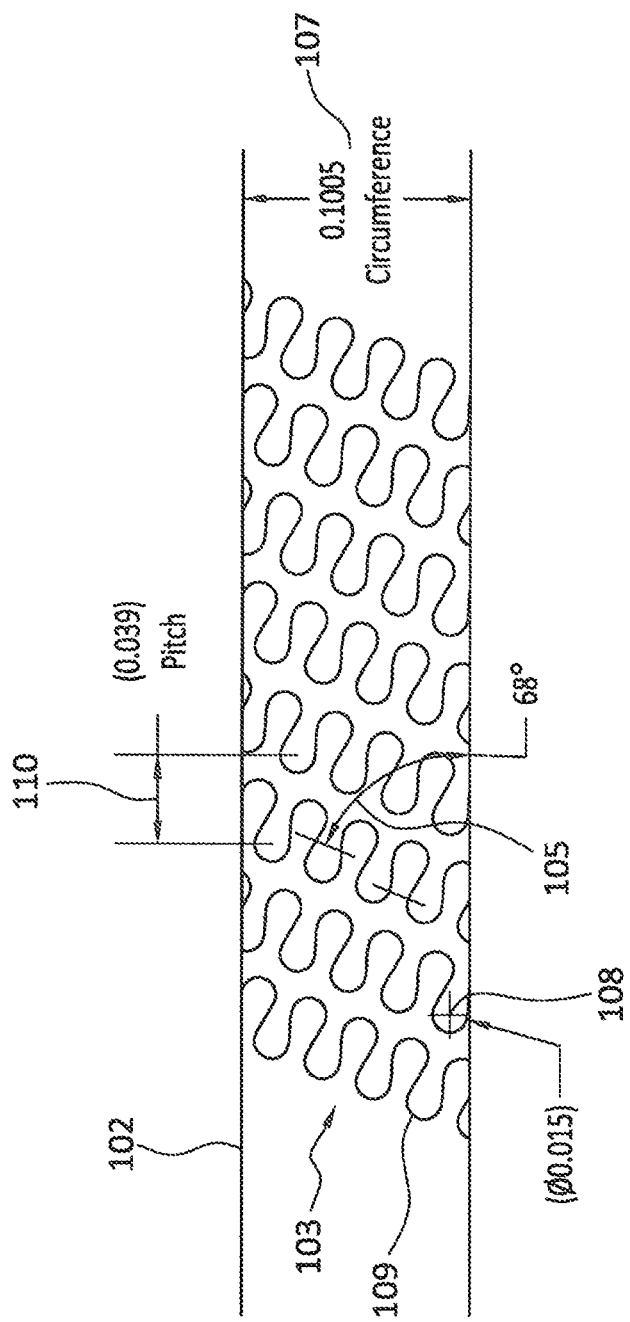
FIGS. 2 and 3 are exploded side views of alternate cut patterns for use in the catheter of FIG. 1 with dimensions by way of example.
Figure 3:
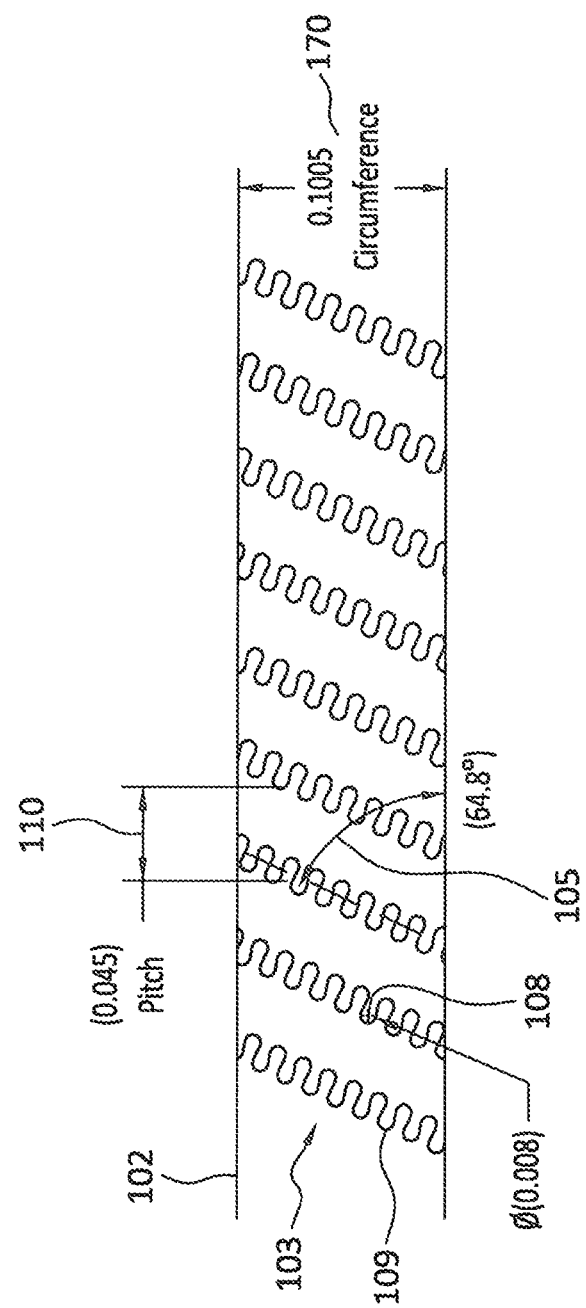

FIGS. 1, 1A and 1E show a preferred embodiment of catheter tube 102. The overall length 155 of tube 102 is shown for example as 61.3 inches, it being understood that solid section 157, shown as 8 inches in length, includes a portion which is gripped for laser cutting; end portion 157 is shortened considerably after laser cutting (to from 0.5 to 3 inches for example) for connection to a luer device as shown in FIGS. 6 and 7. The finished catheter 100 will typically have an length of 90, 135 or 170 cm, depending on the medical procedure being used.

FIG. 1 indicates two detail portions, the first at 156 for the tube cut pattern shown in FIG. 1A and the other at 158 for the distal end configuration shown in FIG. 1E. FIGS. 1A-D and FIGS. 2 and 3 show alternate embodiments of the tube cut pattern with dimensions in each figure by way of example. Like elements have like reference numerals.

Tube 102 has distal and proximal ends 152 and 150 and a laser cut section 154 there between enabling the transmission of rotary and axial motion from the proximal end to the distal end. The laser cut section 154 comprises a majority, i.e., from about 90 to 95%, of the catheter length and is cut in a continuous helical pattern 103 forming interlocking sinusoidal shaped teeth 109 as shown in FIGS. 1A-D, 2 and 3. The sinusoidal shape is preferred because it facilitates disengaging and reengaging of teeth 109 when the catheter is flexed. Other useful teeth shapes include triangular and square shapes as shown in FIGS. 12 and 13.

As shown in FIGS. 1A-D, 2 and 3, sinusoidal teeth have a diameter 108 in the range of about 0.005 to about 0.015 inch and the helical angle 105 of the center-line of the sinusoidal cut 103 is a constant angle between about 64° and about 75°. The diameter of the interlocking sinusoidal teeth can also be expressed as a percentage of the diameter of tube 102, for example from about 5 to 15%, preferably about 8%, of the diameter of catheter tube 102.

The pitch 110 between adjacent rows of teeth 103 is in the range of about 0.028 to about 0.057 inch. The diameter 108 of teeth 109, helical angle 105 and pitch 110 result in from 4 to 12 repetitions of teeth 109 around the circumference of laser cut section 154.

The outside diameter of tube 102 is in the range of about 0.010 to about 0.052 inch and the wall thickness is about 0.0015 to about 0.005 inch.

Figure 8:
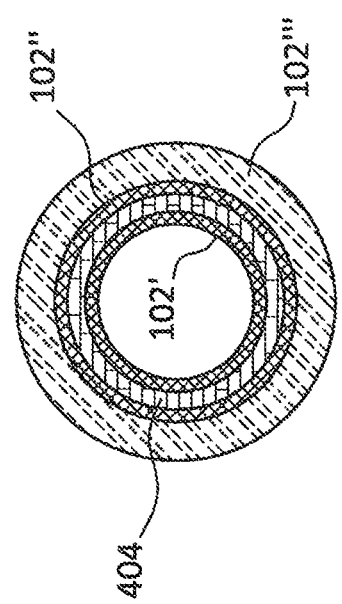
FIG. 8 is a cross section of the catheter of the invention with inner polymer layers and an outer polymer sheath or coating.

FIG. 8 shows the catheter of FIG. 1A in cross section having a polymeric bi-layer of a nylon or like polymer 404 at the interface of catheter tube 102 interior, a Teflon or like polymer 102' forming the interior lumen of the catheter, and a thin nylon or like polymer exterior coating 102".

Proximal end 150 (FIG. 1) comprises an uncut portion 157 configured for coupling to a luer connection (FIGS. 6 and 7). Distal end 152 (FIG. 1E) comprises a solid, uncut section no longer than about 0.02 inch followed by a narrower terminal section no longer than about 0.149 inch in length. Distal end 152 can be narrowed or necked down by compressing end segments 402 created by gusset cuts 401 (FIG. 1E).

In operation, interlocking teeth 109 disengage and reengage in a fish scale manner without undergoing plastic deformation and without substantial polymer separation when the catheter is flexed. The catheter is thus capable of transmitting an axial push force against a vascular occlusion to cross same and allow the catheter to advance beyond the occlusion.

Figure 11:
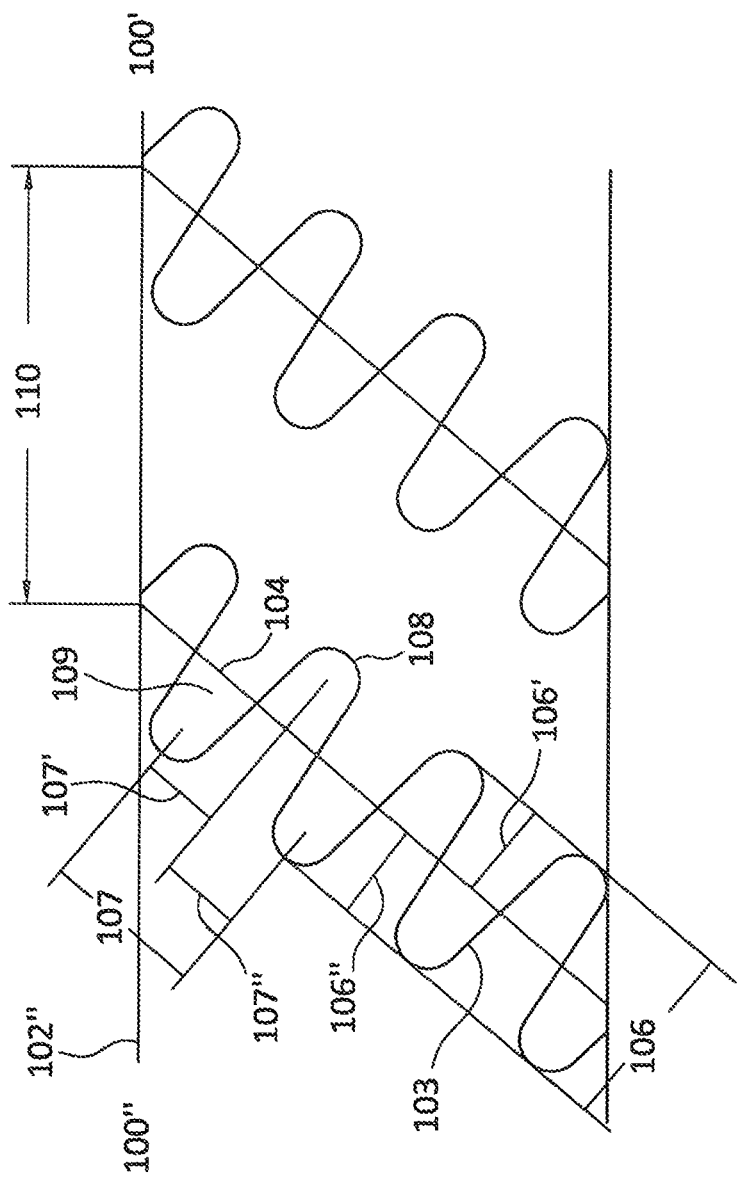

FIG. 11 is a schematic of the metallic tube of the middle layer 102" of the catheter shaft 102 having a distal end 100' and a proximal end 100". The middle metallic layer 102" is comprised of a helical sinusoidal cut pattern 103 drawn from a reference or center-line 104 that is on an angle 105 relative to the longitudinal length of the metallic tube 102". The path of the sinusoidal cut pattern has a peak-to-peak amplitude 106 and period 107. The peak-to-peak amplitude 106 of the cut pattern is split into an amplitude on the distal side of the center-line 106' and an amplitude on the proximal side of the center-line 106". Similarly, the period 107 is split into a distal period 107' and a proximal period 107" as illustrated in FIG. 11. The peaks and valleys of the sinusoidal cut path consist of a peak cut shape 108, which along with the period 107 creates teeth 109 between adjacent peaks or valleys. A pitch 110, the longitudinal spacing from center-line to center-line, is a function of the circumference of the metallic tube 102" and the center-line angle 105. The frequency is calculated by dividing the period 107 from the circumference of the metallic tubing 102".

FIG. 12 shows an alternate embodiment of the cut pattern in FIG. 11, in which the frequency is decreased and the peak cut shape 108 is primarily triangular. The peak cut shape 108 creates teeth 109 that effectively interlock the metallic tubing on the distal and proximal sides of the cut providing increased torque response of the catheter.

FIG. 13 shows an alternate embodiment of the cut pattern in FIG. 11, in which the frequency is increased and the peak cut shape 108 is primarily a square. The peak cut shape 108 creates teeth 109 that effectively interlock the metallic tubing on the distal and proximal sides of the cut providing increased torque response of the catheter.

Figure 14:
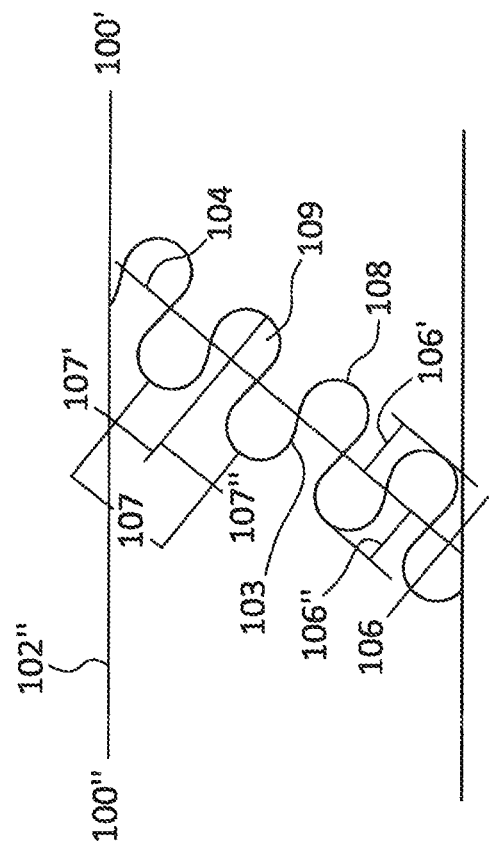

FIG. 14 shows an alternate embodiment of the cut pattern in FIG. 11, in which the distal period 107' and the proximal period 107" are not symmetric. Additionally, the peak cut shape 108 is drawn at a large diameter that along with the distal period dimension 107' creates teeth 109 between adjacent peaks and valleys that effectively interlock the metallic tubing on the distal and proximal sides of the sinusoidal cut providing increased torque response of the catheter.

Figure 15:
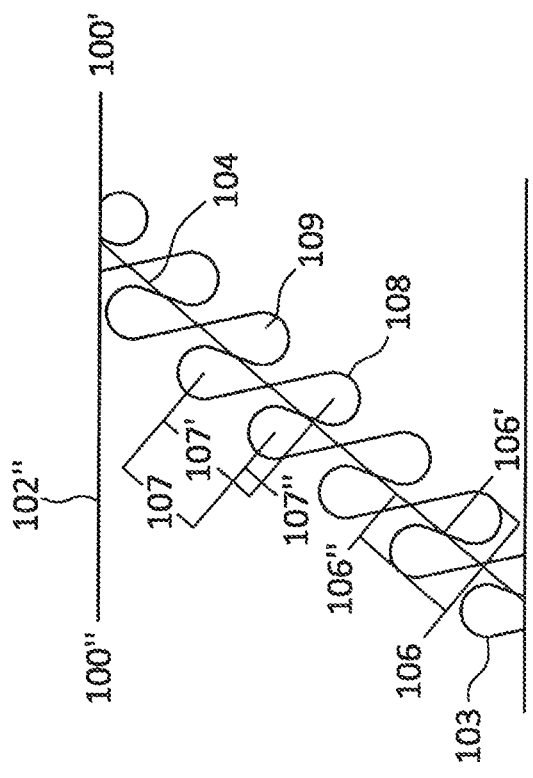

FIG. 15 shows an alternate embodiment of the cut pattern in FIG. 11 in which the distal period 107' is greater than the period 107 and the proximal period 107" is equal to the difference between the distal period 107' and the period 107. The shown cut pattern orients the interlocking features primarily in the circumferential direction instead of the longitudinal direction (as shown in previous schematics) to prevent fish-scaling or hinging of the teeth 109 when the catheter is wrapped around a tight bend.

Figure 16:
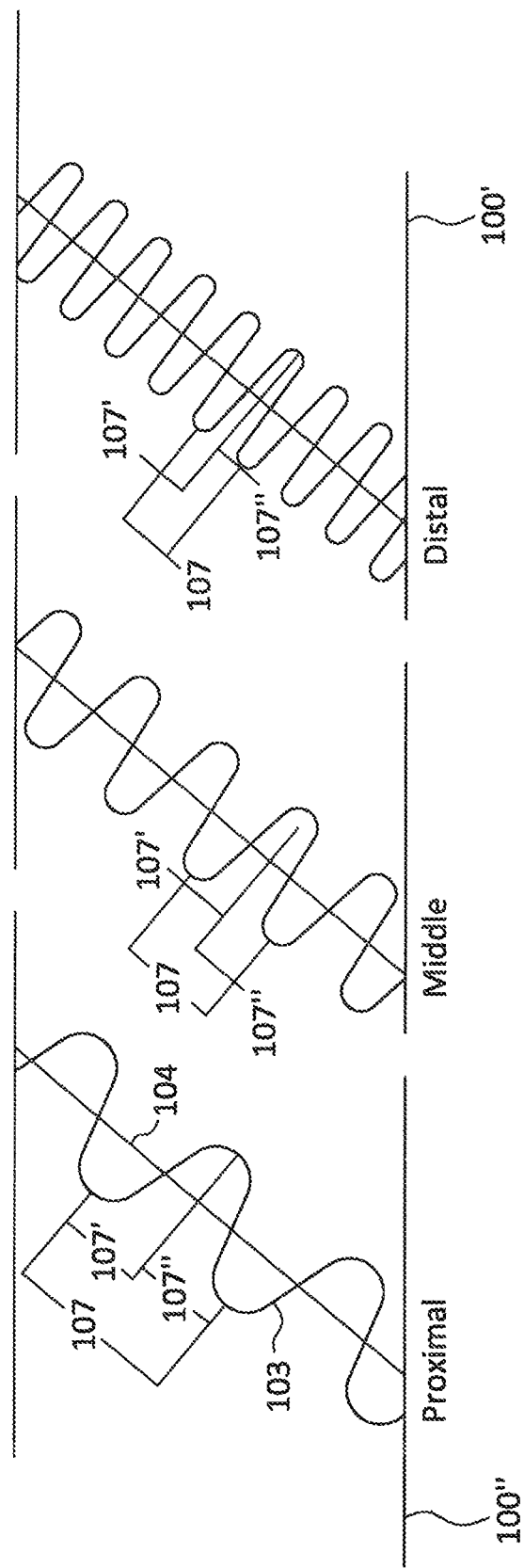

FIG. 16 shows a cut pattern 103, in which the period 107 decreases and the frequency increases along the length of the catheter from proximal 100" to distal 100'.

Figure 17:
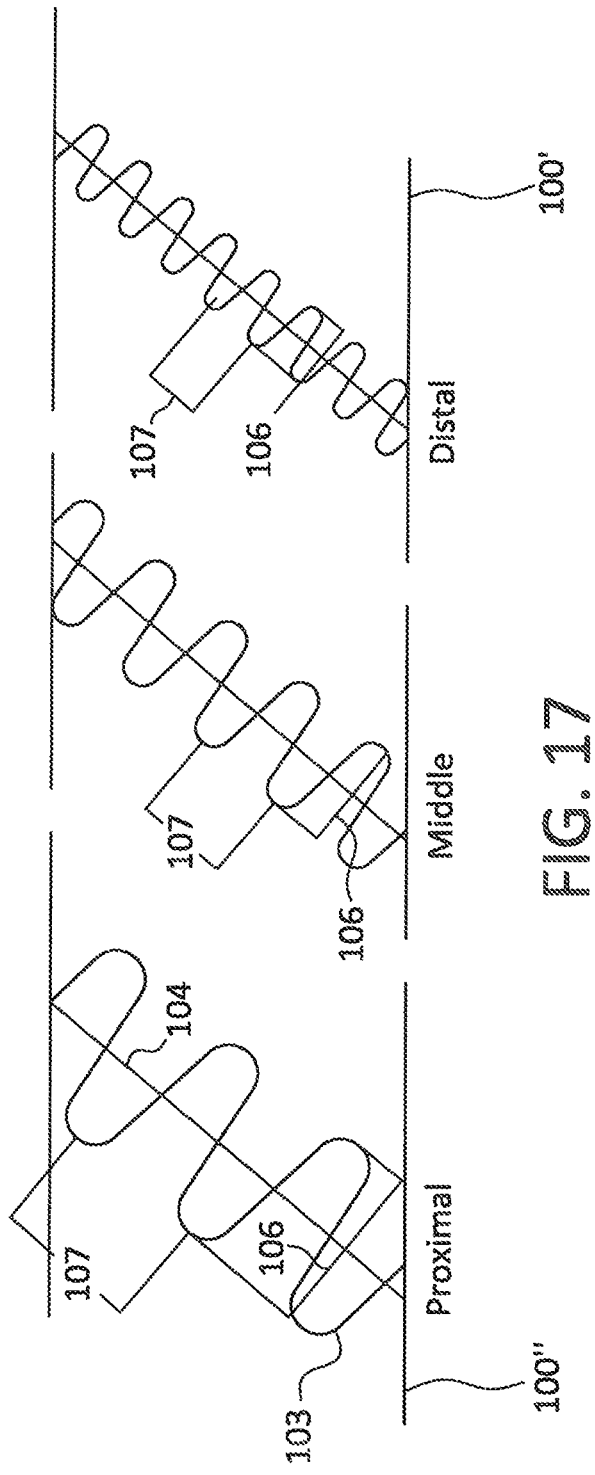

FIG. 17 shows a cut pattern 103, in which the period 107 and peak-to-peak amplitude 106 both decrease along the length of the catheter from proximal 100" to distal 100'.

The distal portions of the catheter can have a cutting feature or features which can be part of the catheter or a separate cannula that goes either over the outside diameter of the catheter or inside the diameter of the catheter.

A perfusion feature can be added to the catheter which enable the physician to flow liquid from the proximal end (outside of the body) to the distal end or a location or locations along the length of the catheter (FIGS. 6 and 7).

Another embodiment is a cut pattern similar to that shown in FIGS. 16 and 17 where the peak-to-peak amplitude 106 decreases while the period 107 remains constant.

In all embodiments, the helical angle could decrease or more likely increase from the proximal end to the distal end, or portions thereof including a center section. The helical angle shown in most drawings is 105 degrees, strictly as an example. Another example, the helical angle could start as 70 degrees and finish more distally at 112 degrees where the rate of angle change can be constant along the length or is variable. In all embodiments, the catheter can be used for CTO, partially blocked vessels, or other vessels or channels within a mammalian body. CTO is used as a difficult example or worst case under which the invention could need to perform if put into practice.

An important aspect of polymeric layers 102', 102" and 404 (FIG. 8) on both the inside diameter is the ability to greatly reduce "fish-scaling". Fish-scaling is the occurrence of a portion of a tube sticking out of surface of a bend or radius similar to how scales on a fish may protrude if the fish were bent at its half point in its body. Fish-scaling is an occurrence seen in stents that are not fully connected and can result in vessel damage. The reduction of fish-scaling can increase the torqueability, flexibility or other attributes of a catheter depending on the tradeoffs decided in a given design. An interruption of the cover 102" or a partial cover can allow an exit point or perfusion of a liquid. The material of cover 102" can be a polymer or a polymer ceramic or a polymer with metal component such as heat shrunk TEFLON®, PEEK (polyether ether ketone), a combination of both, other like polymers and composites. The sealing or encapsulation material can be heat shrunk, sprayed or flowed onto cut tube 102. The material could also have some radiopaque materials added on some or all of the covering material.

A specific application of catheter 100 includes supporting a guidewire or catheter while crossing plaque buildup where the plaque creates a partial blockage or a total blockage also referred to as a chronic total inclusion (CTO).

Other applications which can use catheter 100 include bone reamers and shafts for many surgery devices requiring articulated segments.

EXAMPLES

Set of three catheters in the Table 1 were tested for flexibility and peak axial push force (lbf) and compared to commercially available catheters (described below) using simulation test apparatus shown in FIG. 9. Track tube 510 simulates the iliac arch and its five turns or bends at 510A-E. Track 510 is connected to bifurcated luer 512 for receiving catheter tube 100 which is fed over a guidewire into track 510 via traveling block 505 and tube 511 which carries collet 508 for gripping catheter 100 while it is pushed through track 510 by advancing block 505 via screw arm 506 which is driven by crank 507. Body temperature water is flowed over catheter tube 100 via water line 509 connected to luer 512. Peak push force is measure by pushing catheter 102 against pressure point 513' of load cell 513, Model MBD-100, and sent to digital reader Model SSI, both made by Transducer Techniques.

TABLE 1

| FIG. No. | Guidewire Compatibility | Outer Catheter Diameter | Tubing Wall Thickness |
|---|---|---|---|
| 1B | 0.014" | 2.9 Fr (0.034") | 0.0015" |
| 1A | 0.018" | 3.16 Fr (0.038") | 0.0015" |
| 1C | 0.035" | 4.46 Fr (0.055") | 0.00225" |
| 3 | 0.018" | 3.16 Fr (0.038") | 0.0015" |
| 2 | 0.018" | 3.16 Fr (0.038") | 0.0015" |

Formula for Scaling a Design:

$$(D_1/D_2)(T_1)=T_2$$

$D_1$=Diameter of desired tubing size
$D_2$=Diameter of current tubing size
$T_1$=Current tooth diameter
$T_2$=New tooth diameter $$(T_2/T_1)P_1=P_2$$

$T_1$=Current tooth diameter
$T_2$=New tooth diameter
$P_1$=Current Pitch
$P_2$=New Pitch
Maintain cut angle
OR
Follow the above when scaling down, but when scaling up:
Maintain tooth diameter and cut angle
Increase number of repetitions:

$$(D_1/D_2)(R_1)=R_2$$

$D_1$=Diameter of desired tubing size
$D_2$=Diameter of current tubing size
$R_1$=Current number of Repetitions
$R_2$=New number of repetitions
Adjust pitch as necessary to create a continuous pattern.
Pushability Test Protocol 1) Track an appropriately sized guidewire through the simulated use model.
2) Flush the catheter with saline then track it over the guidewire through the simulated use model until the distal end is close to, but not contacting the load cell.
3) Retract the distal end of the guidewire ~6" from the distal end of the simulated use model.
4) Clamp the system in place with the collet ~1.5" from the entrance to the simulated use model and mark the system just distal to the collet to ensure it does not slip in the fixture during testing.
5) Zero the force gauge then rotate the crank arm until the load cell is preloaded to 0.05 lb+/−0.003.
6) Set the force gauge to peak and rotate the crank arm 3 full rotations (360° each). This constitutes one push. Each 360° rotation of the pusher arm translates the system ⅛" in the distal direction. Record the peak push force then rotate the arm 3 more times for push two and, again, record the peak force. Continue this method for 5 pushes or until the distal end of the system kinks.

Figure 9:
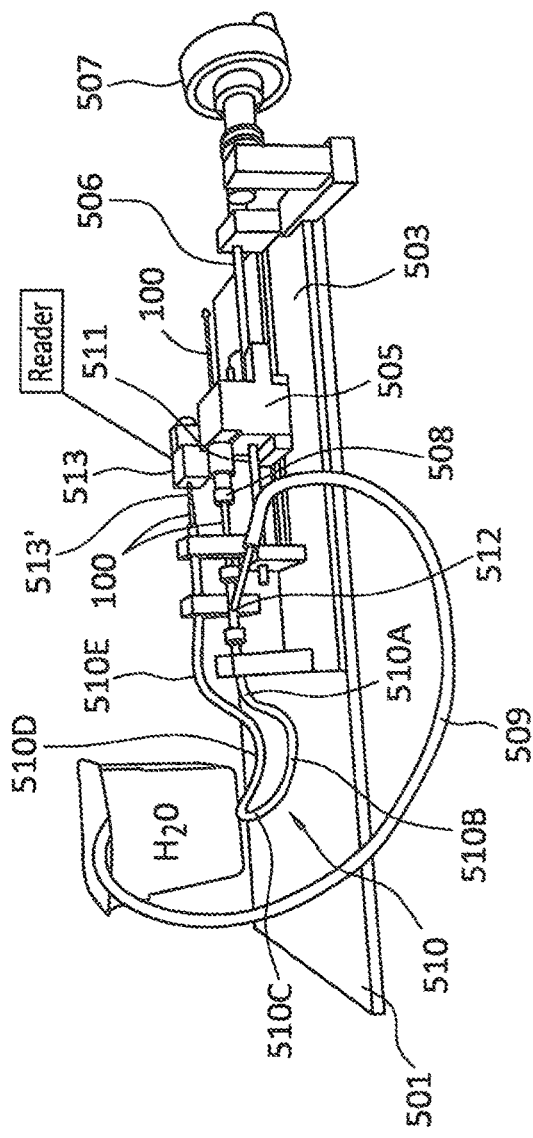
FIG. 9 is a perspective view of test apparatus used to ascertain flexibility and measure axial push force.

Commercial catheters, 3 of each design, were tested against the Table 1 catheters in the test apparatus of FIG. 9 following the same pushability protocol as above:

Control 1: A Cook CXI catheter which is a braided steel catheter (2.6 French) described as the MinaFlex 18 Microcatheter in a 510 (k) premarket notification summary submitted to the FDA by Cook International on Nov. 9, 2007 and available online from the FDA database (Ref. K072724).

Control 2: A Spectranetics Quick-Cross Support Catheter (2.1 French) which is a braided steel catheter described in a 510 (k) premarket notification summary submitted to the FDA by Spectranetics Corporation on Nov. 3, 2003 and available online from the FDA database (Ref. K033678).

Figure 18:
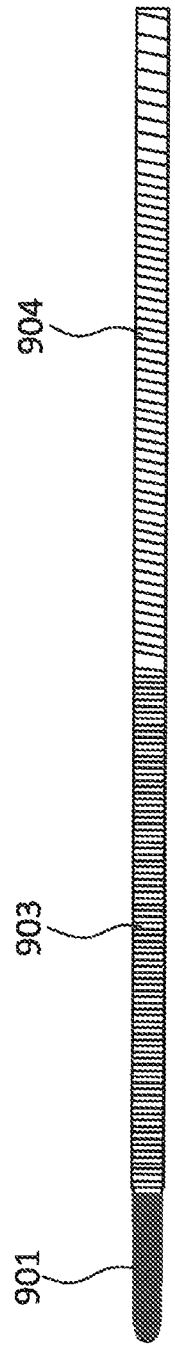
FIG. 18 is a sketch of a commercial catheter tested as a control against catheters of the invention.

Control 3: A Medtronic Total Across catheter which is a spiral cut stainless steel catheter (2.3 French) described in a 510 (k) premarket notification summary submitted to the FDA by Medtronic Vascular on Nov. 15, 2013 and available online from the FDA database (Ref. K133539) and depicted in FIG. 18 (drawn from a product brochure) with polymeric distal tip 901 and spiral windings 903 and 904.

Figure 10:
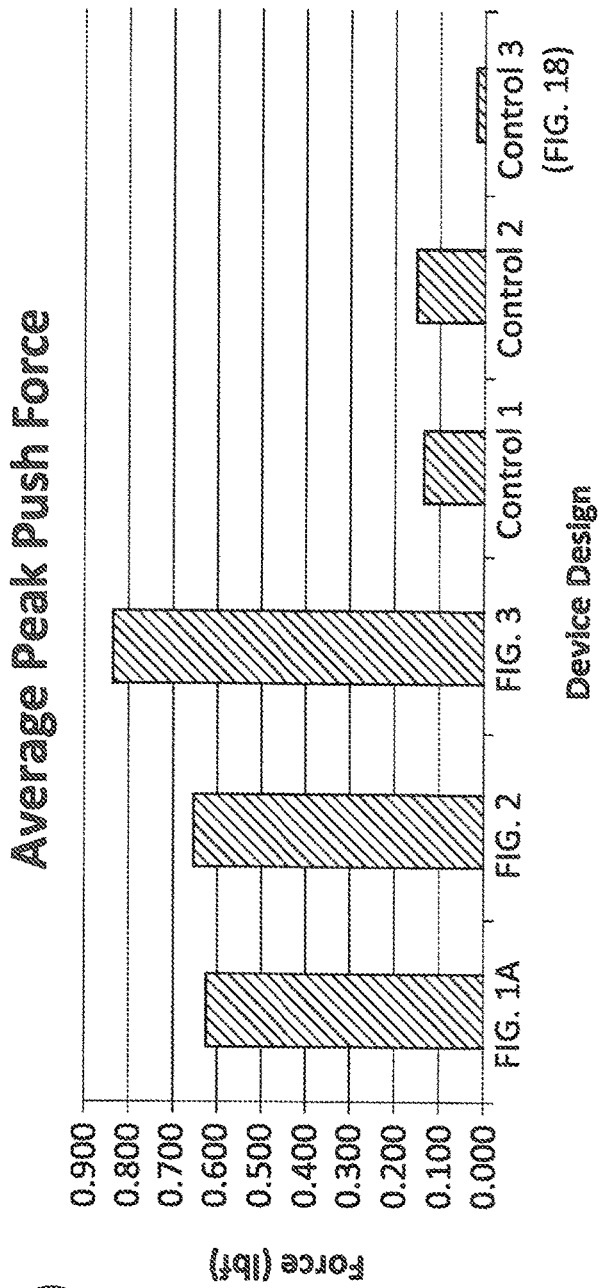
FIG. 10 is a bar graph of average peak push force measured with the test apparatus shown in FIG. 9.

Test results are summarized in the bar graph of FIG. 10 wherein catheters according to the invention (FIGS. 1A, 2 and 3) demonstrated average peak push force values on the order of 4 to 5 times higher than the control catheters.

While this invention has been described as having preferred sequences, ranges, ratios, steps, order of steps, materials, structures, symbols, indicia, graphics, color scheme(s), shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the claims appended hereto or presented later. The invention, therefore, is not limited to the preferred embodiment(s) shown/described herein.

The features of the invention include:

1. Flexible catheter comprising an elongated tube having distal and proximal ends and a laser cut section there between enabling the transmission of rotary and axial motion from the proximal end to the distal end, a. said laser cut section comprising a majority of the catheter length and being cut in a continuous helical pattern forming interlocking teeth wherein: i. the interlocking teeth have a diameter of about 0.005 to about 0.015 inch; ii. the helical angle of the center-line of the helical cut is a constant angle between about 64° and about 75°; iii. the pitch between adjacent rows of teeth is in the range of about 0.028 to about 0.057 inch, the diameter of said teeth, said helical angle and said pitch resulting in from 4 to 12 repetitions of said teeth around the circumference of the laser cut section; and iv. the outside diameter of said tube is in the range of about 0.010 to about 0.052 inch and the wall thickness is about 0.0015 to about 0.005 inch; b. the interior of said tube having a polymeric bi-layer of a nylon or like polymer at the interface of the tube interior and a Teflon or like polymer forming the interior lumen of the catheter; c. the exterior of said tube having a thin nylon or like polymer coating; d. said proximal end comprising an uncut portion of the tube configured for coupling to a luer connection; e. said distal end comprising a solid, uncut section no longer than about 0.02 inch followed by a narrower terminal section no longer than about 0.149 inch in length; and f. whereby said interlocking teeth disengage and reengage in a fish scale manner without undergoing significant plastic deformation and without substantial polymer separation when the catheter is flexed, and whereby said catheter is capable of transmitting an axial, push force against a vascular occlusion to cross same and allow the catheter to advance beyond the occlusion.

2. Flexible catheter of claim 1 wherein the sinusoidal teeth have a diameter of about 0.008 inch.

3. Flexible catheter of claim 1 wherein the outside diameter of said tube is in the range of about 0.017 to about 0.052 inch.

4. Flexible catheter of claim 1 wherein the thickness of the exterior polymer coating is from about 0.0015 to about 0.004 inch.

5. Flexible catheter of claim 4 wherein the thickness of said exterior polymer coating is about 0.003 inch.

6. Flexible catheter of claim 1 wherein the exterior polymer coating blends with the interior nylon polymer through said helical cut.

7. Flexible catheter of claim 1 wherein the laser cut section comprises from about 95 to about 99 percent of the catheter length.

8. Flexible catheter of claim 1 wherein the helical angle of the center-line of the sinusoidal cut is a constant angle between about 68° and about 70°.

9. Flexible catheter of claim 1 wherein the pitch between adjacent teeth is in the range of about 0.033 to about 0.039 inch.

10. Flexible catheter of claim 1 wherein the interior nylon polymer and the exterior nylon polymer coating are a polyether block amide with a Durometer index between 35 and 72.

11. Flexible catheter of claim 1 wherein the interior polymer bi-layer is about 0.0025 inch thick.

12. Flexible catheter of claim 1 wherein the Teflon polymer forming the lumen of said catheter is polytetrafluoroethylene (PTFE) having a static coefficient of friction in the range of 0.05 to 0.08.

13. Flexible catheter of claim 12 wherein the PTFE is about 0.0005 to about 0.001 inch thick.

14. Flexible catheter of claim 1 wherein the catheter tube is full hard 304 stainless steel.

15. Flexible catheter of claim 1 wherein said proximal end is adapted to allow perfusion of the catheter.

16. Flexible catheter of claim 1 wherein the tube is nitinol, steel or other biocompatible metal.

17. Flexible catheter of claim 1 wherein the tube is a polymer or polymer derivative.

18. Flexible catheter of claim 1 which includes a biocompatible hydrophilic coating at least at said distal end.

19. Flexible catheter of claim 1 wherein said proximal end includes a fitting to facilitate guidewire access through the catheter.

20. Flexible catheter of claim 1 wherein the catheter contains holes or slits near the distal end to allow perfusion of liquid.

21. Flexible catheter of claim 1 wherein the narrower terminal section of the distal end includes one or more V-shaped cuts for tapering the terminal section.

22. Flexible catheter of claim 1 wherein the interlocking teeth are sinusoidal, triangular or square shaped.

23 Flexible catheter tube comprising an elongated tube having distal and proximal ends and a laser cut section there between, said catheter in cross section comprising: a. an inside tube diameter of not less than about 0.010 inch and a tube wall thickness of about 0.0015 to 0.005 inch; b. a polymeric bi-layer of a nylon polymer at the interface of the tube interior and a Teflon polymer forming the interior lumen of the catheter; and c. a thin nylon polymer exterior coating.

24. Flexible catheter of claim 23 wherein the exterior coating blends with the interior nylon polymer through said laser cut.

25. Flexible catheter of claim 23 wherein said wall thickness is about 0.0015 inch.

26. Flexible catheter of claim 23 wherein the exterior coating has a thickness from about 0.0015 to about 0.003 inch.

27. Flexible catheter of claim 23 wherein the interior nylon polymer and the exterior nylon polymer coating are a polyether block amide with a Durometer index between 35 and 72.

28. Flexible catheter of claim 23 wherein the Teflon polymer forming the lumen of said catheter is polytetrafluoroethylene having a static coefficient of friction in the range of 0.05 to 0.08.

29. Process for resolving total or partial body lumen blockages which comprises inserting a catheter into body lumen having a blockage at a distal location, said catheter comprising an elongated tube having distal and proximal ends and a laser cut section there between, a. said laser cut section comprising a majority of the catheter length and being cut in a continuous helical pattern forming interlocking sinusoidal shaped teeth wherein: i. the sinusoidal teeth have a diameter of about 0.007 to about 0.015 inch; ii. the helical angle of the center-line of the sinusoidal cut is a constant angle between about 64° and about 75°; iii. the pitch between adjacent teeth is in the range of about 0.028 to about 0.057 inch, the diameter of said teeth, said helical angle and said pitch resulting in from 4 to 12 repetitions of said teeth around the circumference of the laser cut section; and iv. the outside diameter of said tube is in the range of about 0.010 to about 0.052 inch and the wall thickness is about 0.0015 to about 0.005inch; b. the interior of said tube having a polymeric bi-layer of a nylon polymer at the interface of the tube interior and a Teflon polymer forming the interior lumen of the catheter; c. the exterior of said tube having a thin nylon polymer coating; d. said proximal end comprising an uncut portion of the tube configured for coupling to a luer connection; e. said distal end comprising a solid, uncut section no longer than about 0.02 inch followed by a narrower terminal section no longer than about 0.149 inch in length; f. advancing said catheter through said body lumen until said distal end encounters the blockage, said interlocking teeth disengaging and reengaging in a fish scale pattern without undergoing significant plastic deformation and without substantial polymer separation when the catheter is flexed during advancement through the body lumen, and g. transmitting an axial, push force from the proximal end of the catheter to the distal end to cross the blockage and allow the catheter to advance therebeyond.

What is claimed is:

1. A flexible catheter capable of transmitting an axial push force against a vascular occlusion thereby allowing said catheter to advance beyond said occlusion, said catheter comprising an elongated tube having an exterior, an internal lumen, a wall thickness, an outside diameter, a circumference, a distal end, a proximal end and a laser cut section between said distal and proximal ends, said laser cut section enabling transmission of rotary and axial motion from said proximal end to said distal end,
   a. said catheter having a length such that said laser cut section comprises substantially 90 to 99 percent of said length of said catheter, wherein said laser cut section comprises a helical cut in a continuous helical pattern forming rows of interlocking teeth, said helical cut having a center line and a helical cut angle, wherein:
      i. said interlocking teeth have a diameter substantially in a range of 0.005 to 0.015 inch and a pitch between said rows of interlocking teeth that is constant along said laser cut section;
      ii. said helical cut angle is a constant angle along said laser cut section, said constant angle is substantially between 64° and 75°;
      iii. said pitch is substantially in a range of 0.028 to 0.057 inch, said diameter of said interlocking teeth, said helical cut angle and said pitch resulting in from 4 to 12 repetitions of said interlocking teeth around said circumference; and
      iv. said outside diameter of said tube is substantially in a range of 0.024 to 0.055 inch and said wall thickness is substantially in a range of 0.0015 to 0.005 inch;
   b. said internal lumen of said tube having a layer of a nylon or nylon polymer at said internal lumen and a Teflon or Teflon polymer layer over said nylon or nylon polymer layer;
   c. said exterior of said tube having an exterior polymer coating of a nylon or nylon polymer which enables said catheter to flex without deformation or substantial separation of said exterior polymer coating;
   d. said proximal end comprising an uncut portion of said tube and configured for coupling to a luer connection; and
   e. said distal end comprising a distal section that is solid and uncut and a narrowed terminal section, wherein said distal section is substantially no longer than 0.02 inch in length and said narrower terminal section is substantially no longer than 0.149 inch in length.

2. The flexible catheter of claim 1 wherein said interlocking teeth have a diameter of substantially 0.008 inch.

3. The flexible catheter of claim 1 wherein said outside diameter of said tube is substantially in a range of 0.017 to 0.052 inch.

4. The flexible catheter of claim 1 wherein said exterior polymer coating has a thickness substantially in a range of 0.0015 to 0.004 inch.

5. The flexible catheter of claim 4 wherein said exterior polymer coating has a thickness of substantially 0.003 inch.

6. The flexible catheter of claim 1 further comprising space between adjacent interlocking teeth such that said exterior polymer coating blends with said nylon or nylon polymer layer at said internal lumen through said space.

7. The flexible catheter of claim 1 wherein said laser cut section comprises substantially 95 to 99 percent of said length of said catheter.

8. The flexible catheter of claim 1 wherein said constant angle is substantially between 68° and 70°.

9. The flexible catheter of claim 1 wherein said pitch is substantially in a range of 0.033 to 0.039 inch.

10. The flexible catheter of claim 1 wherein said nylon or nylon polymer layer at said internal lumen and said exterior polymer coating are a polyether block amide with a Durometer index between 35 and 72.

11. The flexible catheter of claim 1 wherein a thickness of said nylon or nylon polymer layer at said internal lumen is substantially 0.0025 inch.

12. The flexible catheter of claim 1 wherein said Teflon or Teflon polymer layer is polytetrafluoroethylene (PTFE) having a static coefficient of friction in a range of 0.05 to 0.08.

13. The flexible catheter of claim 12 wherein a thickness of said PTFE is substantially in a range of 0.0005 to 0.001 inch.

14. The flexible catheter of claim 1 wherein said tube is full hard 304 stainless steel.

15. The flexible catheter of claim 1 wherein said catheter is adapted to allow perfusion.

16. The flexible catheter of claim 1 wherein said tube is nitinol, steel or other biocompatible metal.

17. The flexible catheter of claim 1 wherein said tube is a polymer or polymer derivative.

18. The flexible catheter of claim 1 further comprising a biocompatible hydrophilic coating at least at said distal end.

19. The flexible catheter of claim 1 wherein said proximal end includes a fitting to facilitate guidewire access through said catheter.

20. The flexible catheter of claim 1 wherein said narrower terminal section includes one or more V-shaped cuts.

21. The flexible catheter of claim 1 wherein said interlocking teeth are sinusoidal, triangular or square shaped.

22. A process for resolving total or partial body lumen blockages, said process comprising inserting a catheter into a body lumen having a blockage, said catheter comprising an elongated tube having an exterior, an internal lumen, a wall thickness, an outside diameter, a circumference, a distal end, a proximal end and a laser cut section between said distal and proximal ends, said laser cut section enabling the transmission of rotary and axial motion from said proximal end to said distal end,
   a. said catheter having a length such that said laser cut section comprises substantially 90 to 99 percent of said length of said catheter, wherein said laser cut section comprises a helical cut in a continuous helical pattern forming rows of interlocking teeth, said helical cut having a center line and a helical cut angle, wherein:
      i. said interlocking teeth have a diameter substantially in a range of 0.005 to 0.015 inch and a pitch between said rows of interlocking teeth that is constant along said laser cut section;
      ii. said helical cut angle is a constant angle along said laser cut section, said constant angle is substantially between 64° and 75°;
      iii. said pitch is substantially in a range of 0.028 to 0.057 inch, said diameter of said interlocking teeth, said helical cut angle and said pitch resulting in from 4 to 12 repetitions of said interlocking teeth around said circumference; and
      iv. said outside diameter of said tube is substantially in a range of 0.024 to 0.055 inch and said wall thickness is substantially in a range of 0.0015 to 0.005 inch;
   b. said internal lumen of said tube having a layer of a nylon or nylon polymer at said internal lumen and a Teflon or Teflon polymer layer over said nylon or nylon polymer layer;
   c. said exterior of said tube having an exterior polymer coating of a nylon or nylon polymer which enables said catheter to flex without deformation or substantial separation of said exterior polymer coating;
   d. said proximal end comprising an uncut portion of said tube and configured for coupling to a luer connection;
   e. said distal end comprising a distal section that is solid and uncut and a narrower terminal section, wherein said distal section is substantially no longer than 0.02 inch in length and said narrower terminal section is substantially no longer than 0.149 inch in length; and
   said process comprising transmitting an axial push force from the proximal end to said distal end to cross said blockage and allow said catheter to advance there beyond.

23. The process of claim 22 wherein said blockage is a chronic total occlusion with or without one or more hard end caps.

* * * * *